US012025858B2

(12) United States Patent
Tai et al.

(10) Patent No.: US 12,025,858 B2
(45) Date of Patent: Jul. 2, 2024

(54) CONTACT LENS WITH METERED LIQUID SYSTEM

(71) Applicants: California Institute of Technology, Pasadena, CA (US); University of Southern California, Los Angeles, CA (US)

(72) Inventors: Yu-Chong Tai, Pasadena, CA (US); Nicholas E. Scianmarello, Pasadena, CA (US); Charles M. T. DeBoer, Pasadena, CA (US); Mark S. Humayun, Glendale, CA (US)

(73) Assignees: California Institute of Technology; University of Southern California

( * ) Notice: Subject to any disclaimer, the term of this patent is extended or adjusted under 35 U.S.C. 154(b) by 615 days.

(21) Appl. No.: 17/013,759

(22) Filed: Sep. 7, 2020

(65) Prior Publication Data

US 2020/0409177 A1    Dec. 31, 2020

Related U.S. Application Data

(63) Continuation of application No. 16/017,667, filed on Jun. 25, 2018, now Pat. No. 10,768,444, which is a
(Continued)

(51) Int. Cl.
*G02C 7/04* (2006.01)
*G02C 7/08* (2006.01)
*A61K 9/00* (2006.01)

(52) U.S. Cl.
CPC ............... *G02C 7/049* (2013.01); *G02C 7/04* (2013.01); *G02C 7/041* (2013.01); *G02C 7/085* (2013.01); *A61K 9/0051* (2013.01)

(58) Field of Classification Search
CPC .......... G02C 7/049; G02C 7/04; G02C 7/041; G02C 7/085; A61K 9/0051
See application file for complete search history.

(56) References Cited

U.S. PATENT DOCUMENTS 1,543,506 A   6/1925  Miller
3,515,095 A   6/1970  Baranow et al.
(Continued)

FOREIGN PATENT DOCUMENTS

CN    101616640       12/2009
CN    102316833 A      1/2012
(Continued)

OTHER PUBLICATIONS

EP19820418.2, "Extended European Search Report", dated Feb. 15, 2022, 9 pages.
(Continued)

*Primary Examiner* — Mustak Choudhury
(74) *Attorney, Agent, or Firm* — Mark P. Mathison

(57) ABSTRACT

A contact lens fluid delivery device having a liquid reservoir connected to a channel with a flow regulator is described. Other eye hydration and variable dioptric power contact lenses are described herein. Also described are implantable liquid delivery apparatuses having a liquid storage reservoir connected to a channel with a flow regulator. These devices and apparatuses are useful for specific, targeted delivery of therapeutic liquids within a subject. In some embodiments, the devices incorporate actuation chambers which provide a driving force releasing the fluid into the targeted area e.g., the eye. The actuation chambers described herein can contain phase change materials or osmotic chambers or a combination thereof to drive the release of fluid.

20 Claims, 8 Drawing Sheets

Related U.S. Application Data continuation of application No. 14/881,935, filed on Oct. 13, 2015, now Pat. No. 10,031,348.

(60) Provisional application No. 62/152,518, filed on Apr. 24, 2015, provisional application No. 62/131,476, filed on Mar. 11, 2015, provisional application No. 62/064,339, filed on Oct. 15, 2014.

(56) References Cited

U.S. PATENT DOCUMENTS

| | | | |
|---|---|---|---|
| 4,572,846 | A | 2/1986 | Foss et al. |
| 4,942,018 | A | 7/1990 | Munk |
| 5,393,103 | A | 2/1995 | Cretzler |
| 5,472,436 | A | 12/1995 | Fremstad |
| 5,534,068 | A | 7/1996 | Beach et al. |
| 7,699,464 | B2 * | 4/2010 | Iuliano .................. G02C 7/041 623/6.13 |
| 8,133,512 | B2 | 3/2012 | Kunzler et al. |
| 8,372,046 | B2 | 2/2013 | Meng et al. |
| 8,404,265 | B2 | 3/2013 | Chauhan et al. |
| 8,404,271 | B2 | 3/2013 | Byrne et al. |
| 8,623,400 | B2 | 1/2014 | Liu et al. |
| 8,663,194 | B2 | 3/2014 | Ambati et al. |
| 9,086,580 | B2 | 7/2015 | Grant et al. |
| 9,091,865 | B2 | 7/2015 | Hofmann et al. |
| 9,421,126 | B2 | 8/2016 | Alster et al. |
| 9,655,774 | B2 | 5/2017 | Tai et al. |
| 9,763,825 | B2 | 9/2017 | Tai et al. |
| 9,782,346 | B2 | 10/2017 | Venkatraman et al. |
| 9,937,073 | B2 | 4/2018 | de Juan, Jr. et al. |
| 10,031,348 | B2 | 7/2018 | Tai et al. |
| 10,092,387 | B2 | 10/2018 | Tai et al. |
| 10,768,444 | B2 | 9/2020 | Tai et al. |
| 11,051,977 | B2 | 7/2021 | Tai et al. |
| 11,077,462 | B2 | 8/2021 | Tai et al. |
| 2008/0023324 | A1 | 1/2008 | Ban et al. |
| 2008/0035875 | A1 | 2/2008 | Tai et al. |
| 2008/0169427 | A1 | 7/2008 | Hatem et al. |
| 2008/0231799 | A1 | 9/2008 | Iuliano |
| 2008/0286338 | A1 | 11/2008 | Rosenthal et al. |
| 2010/0114309 | A1 | 5/2010 | de Juan, Jr. et al. |
| 2010/0217209 | A1 | 8/2010 | Meng et al. |
| 2011/0116035 | A1 | 5/2011 | Fritsch et al. |
| 2011/0184358 | A1 | 7/2011 | Weiner et al. |
| 2011/0282328 | A1 * | 11/2011 | Ambati .................. A61P 31/04 604/521 |
| 2012/0022473 | A1 | 1/2012 | Shikamura et al. |
| 2012/0115189 | A1 | 5/2012 | Jovanovich et al. |
| 2012/0268712 | A1 * | 10/2012 | Egan .................. G02C 7/04 351/159.34 |
| 2012/0302972 | A1 * | 11/2012 | Higuchi .................. A61F 9/0017 604/290 |
| 2013/0208237 | A1 * | 8/2013 | Hawke .................. G02C 7/049 351/159.36 |
| 2013/0242255 | A1 * | 9/2013 | Caldarise .................. G02C 7/049 351/159.36 |
| 2014/0005514 | A1 | 1/2014 | Pugh et al. |
| 2014/0193045 | A1 | 7/2014 | Otis et al. |
| 2014/0235457 | A1 | 8/2014 | Esfandyarpour et al. |
| 2014/0236006 | A1 | 8/2014 | Omura |
| 2014/0236066 | A1 | 8/2014 | Horvath et al. |
| 2015/0111023 | A1 | 4/2015 | Tai et al. |
| 2015/0293031 | A1 | 10/2015 | Fisk |
| 2016/0109726 | A1 | 4/2016 | Tai et al. |
| 2017/0001195 | A1 | 1/2017 | Unger et al. |
| 2017/0113246 | A1 | 4/2017 | Tai et al. |
| 2017/0136463 | A1 | 5/2017 | Tai et al. |
| 2018/0333298 | A1 | 11/2018 | Tai et al. |

FOREIGN PATENT DOCUMENTS

| | | |
|---|---|---|
| CN | 105435338 A | 3/2016 |
| WO | 2007106557 A2 | 9/2007 |
| WO | 2008083118 | 7/2008 |
| WO | 2010041230 | 4/2010 |
| WO | 2016061125 | 4/2016 |
| WO | 2017070528 | 4/2017 |

OTHER PUBLICATIONS

PCT/US2019/033369, "International Preliminary Report on Patentability", dated Dec. 3, 2020, 8 pages.

PCT/US2019/036498, "International Preliminary Report on Patentability", dated Dec. 24, 2020, 9 pages.

"Compliance Problems with Glaucoma Eye Drops", OpthalmologyWeb, Available Online at: https://www.ophthalmologyweb.com/Featured-Articles/19875-Compliance-Problems-with-Glaucoma-Eye-Drops/, Aug. 23, 2010, 3 pages.

"How to Succeed at Eye Drop Treatment: It's All in Your Hands", Glaucoma Center of Excellence, Available online at: https://www.hopkinsmedicine.org/wilmer/services/glaucoma/book/chapter_how_to_succeed_with_drops.html, Accessed from Internet on Jun. 14, 2019, 7 pages.

"Improving Compliance Through Access to Eye Drop Medication", Available online at: https://www.cameron-graham.co.uk/pages/pharmacists.php, Accessed from Internet on Jun. 14, 2019, 2 pages.

"The Role of the Pharmacist in Improving Glaucoma Compliance", Ear and Eye Care, NI Pharmacy in Focus, Available online at: https://www.cameron-graham.co.uk/pages/pharmacists.php, Aug. 2005, 1 page.

Arai et al., "Long-Term Electroencephalogram Measurement Using Polymer-Based Dry Microneedle Electrode", IEEE, Transducers 2015, Anchorage, Alaska, Jun. 21-25, 2015, pp. 81-84.

Chang et al., "High Yield Packaging for High-Density Multi-Channel Chip Integration of Flexible Parylene Substrate", IEEE, MEMS 2012, Jan. 29-Feb. 2, 2012, pp. 353-356.

Chang et al., "Packaging Study for a 512-Channel Intraocular Epiretinal Implant", IEEE, MEMS 2013, Jan. 20-24, 2013, pp. 1045-1048.

EP16858334.2, "Extended European Search Report", dated Jul. 23, 2019, 8 pages.

Kang et al., "Effects of Deposition Temperature on Parylene-C Properties", IEEE, MEMS 2013, Jan. 20-24, 2013, pp. 389-392.

Kramer et al., "Polymerization of Para-Xylylene Derivatives (Parylene Polymerization). I. Deposition Kinetics for Parylene N and Parylene C", Journal of Polymer Science, Polymer Chemistry Edition, vol. 22, No. 2, Feb. 1984, pp. 475-491.

Metzen et al., "Diffusion Limited Tapered Coating with Parylene C", IFMBE Proceedings 25/IX, 2009, pp. 96-97.

Metzen et al., "Diffusion-Limited Deposition of Parylene C", Journal of Microelectromechanical Systems, vol. 20, No. 1, Feb. 2011, pp. 239-250.

PCT/US2015/055368, "International Preliminary Report on Patentability", dated Apr. 27, 2017, 10 pages.

PCT/US2015/055368, "International Search Report and Written Opinion", dated Feb. 16, 2016, 12 pages.

PCT/US2016/058200, "International Preliminary Report on Patentability", dated May 3, 2018, 12 pages.

PCT/US2016/058200, "International Search Report and Written Opinion", dated Jan. 10, 2017, 13 pages.

PCT/US2019/033369, "International Search Report and Written Opinion", dated Sep. 17, 2019, 11 pages.

PCT/US2019/036498, "International Search Report and Written Opinion", dated Oct. 31, 2019, 12 pages.

Ramachandran et al., "A Study of Parylene C Polymer Deposition Inside Microscale Gaps", IEEE Transactions on Advanced Packaging, vol. 30, No. 4, Nov. 5, 2007, pp. 712-724.

Robin, "Beyond Compliance: Getting the Drops in", Review of Ophthalmology, Available online at: https://reviewofophthalmology.com/article/beyond-compliance-getting-the-drops-in, Feb. 18, 2010, 5 pages.

Sawano et al., "Sealing Method of PDMS as Elastic Material for MEMS", IEEE, MEMS 2008, Jan. 13-17, 2008, pp. 419-422.

(56) References Cited

OTHER PUBLICATIONS

Senkevich et al., "Thermomechanical Properties of Parylene X, A Room-Temperature Chemical Vapor Depositable Crosslinkable Polymer", Chemical Vapor Deposition, vol. 13, No. 1, Jan. 2007, pp. 55-59.
Wang et al., "Reliable Deposition of Ultra-Thin Parylene", IEEE 2016, MEMS 2016, Jan. 24-28, 2016, pp. 462-464.

* cited by examiner

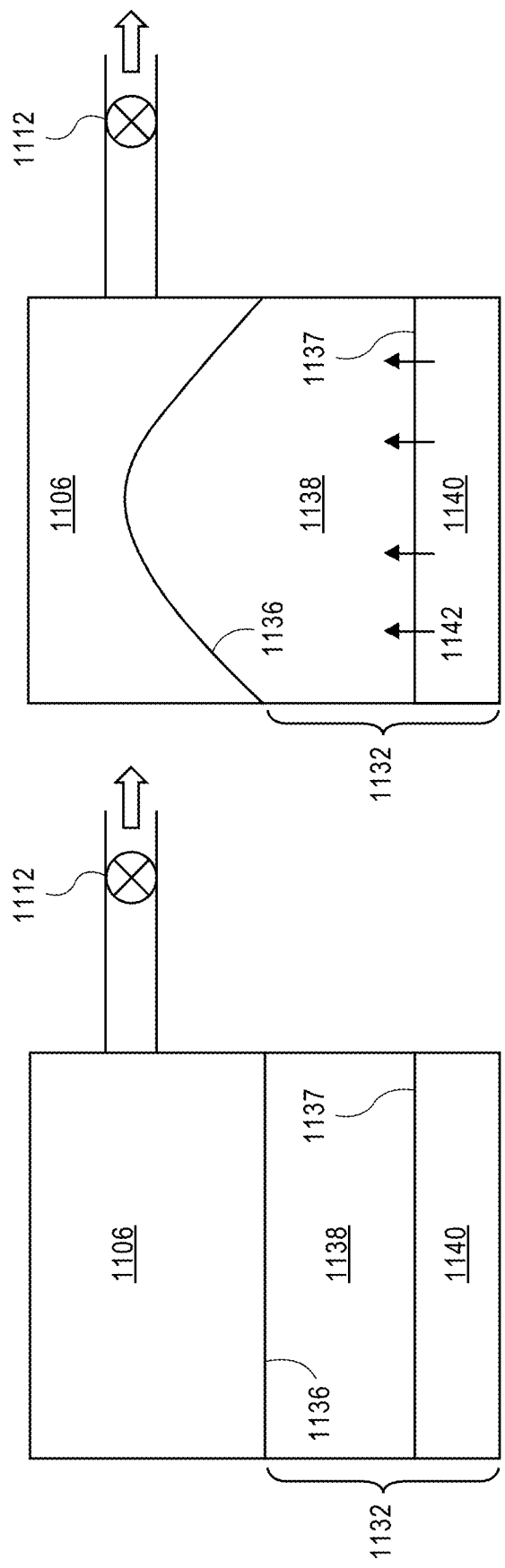

CONTACT LENS WITH METERED LIQUID SYSTEM

CROSS-REFERENCES TO RELATED APPLICATIONS

This application is a continuation of U.S. application Ser. No. 16/017,667 filed Jun. 25, 2018 and issued as U.S. Pat. No. 10,768,444 on Sep. 8, 2020, which is a continuation of U.S. application Ser. No. 14/881,935, filed Oct. 13, 2015 and issued as U.S. Pat. No. 10,031,348 on Jul. 24, 2018, which claims the benefit of U.S. Provisional Application No. 62/152,518, filed Apr. 24, 2015, U.S. Provisional Application No. 62/131,476, filed Mar. 11, 2015, and U.S. Provisional Application No. 62/064,339, filed Oct. 15, 2014, the contents of which are hereby incorporated in their entireties for all purposes.

STATEMENT AS TO RIGHTS TO INVENTIONS MADE UNDER FEDERALLY SPONSORED RESEARCH AND DEVELOPMENT

Not Applicable

BACKGROUND

Generally, embodiments of the present invention related devices for administration of a therapeutic agent (e.g., medicament, drugs, saline, etc.) to a particular part of a patient's body.

One example of targeted delivery to a part of a patient's body is the eye using a contact lens.

The most common treatment for various eye conditions is through topical application of ophthalmic solutions or eye drops. This method of fluid delivery to the eye accounts for 90% of all the ophthalmic medications. This mode of delivery, however, is very inefficient, with sometimes less than 10% absorption in the eye of the medicine from the eye drops. It would be beneficial to be able to deliver ophthalmic fluids and medications more precisely and effectively. Drug eluting contact lenses have been explored, but there remains a need for a contact lenses with a simple design, that is able to effectively provide medication and or lubrication to the eye with a controlled flow rate over time.

Beyond direct delivery to the eye, medical treatment often requires the administration of a therapeutic agent (e.g., medicament, drugs, etc.) to a particular part of a patient's body.

As implantable devices of varying sizes, dosing requirements, and implant locations become available, the reliable delivery of drugs/fluids over long periods of time (i.e. daily, bi-weekly or monthly dosing over two or more years become progressively complicated.

Existing medical equipment actuation and metering systems would be difficult, if not impossible, to miniaturize into a scale that is implantable or that can fit into a contact lens. Most actuation and metering systems require a variety of power sources, electrical systems, and other hardware to function properly. Further, their function often depends on materials that are not biocompatible, for example rare earth metal magnets for motors and solenoids. Static friction, or "stiction," of mechanical elements is also different at smaller scales than it is on a macroscopic scale.

The functionality of many slow response actuation systems (i.e. electro-osmosis electrolysis) based pumps are limited in the fact that for temporally separated doses, each successive dose requires more time and/or power to complete. That is, slow response actuation systems require electrical power over long periods of time—electrical power that drains batteries.

As such, there is a need in the art for improved approaches to targeted drug delivery both in a patient's eye and elsewhere in the body.

BRIEF SUMMARY

Generally, the present invention relates to targeted fluid/drug delivery devices with controlled delivery of fluid and/or drug over time to a specific portion of the body. For example, the device can be a wearable contact lenses, an intraocular lens, an ocular drug pump, an implantable insulin pump, an inner ear pump, a brain pump, and any other implantable or non-implantable pump.

Controlled delivery within these devices can be achieved by using micromachined channel(s) and/or valve(s) that are mechanically actuated by an external pressure, a passive method, or extremely-low amperage electronic means. External pressure can include finger presses by a physician or the subject him or herself. Passive continuous delivery includes capillary action, dissolvable barriers within the device, and/or a pressure gradient. Pressure gradients can be introduced and controlled over time through a subject manually pressing on a predetermined location of the device or through a built in actuation system that increases pressure using, for example, osmotic gradients or phase change materials. Electronic actuation can include using electromagnetic methods for opening a valve or actuating a pump to dispense fluid.

Some embodiments of the present invention relate to an ophthalmic liquid delivery contact lens device. The contact lens includes a transparent optical zone and an annual periphery outside of the optical zone, a therapeutic liquid storage reservoir within the periphery of the contact lens body, a channel from the reservoir within the periphery to an outlet for dispensing liquid to an eye, and a flow regulator connected with the channel.

The contact lens can include a one-way valve connected at an output of the reservoir, and a metering volume with a predetermined capacity for a dose of a therapeutic liquid connected with the channel.

In some embodiments, the flow regulator includes high-fluidic-resistance channel.

The contact lens can include a pressure regulator including a multi-level valve seat, and a floating valve piece configured to mate with the multi-level valve seat. The floating valve piece mates with different levels of the multi-level valve seat depending on pressure, configured to open only between a first predetermined pressure and a second predetermined pressure.

The contact lens can also include a serpentine duct. The serpentine duct can extend tangentially to the contact lens body with a constant radius for each duct portion.

The contact lens can include an actuation chamber, and a flexible diaphragm between the actuation chamber and the reservoir. A heating element can be disclosed within the actuation chamber. A phase change material can be included within the actuation chamber. The phase change material being of a substance such that it expands when converting between a solid to a liquid, a solid to a gas, or a liquid to a gas when warmed. The expansion of the phase change causes bowing of a portion of the diaphragm into the reservoir.

The actuation chamber can also include a semi-permeable membrane that divides the actuation chamber into an osmotic chamber and a fluid chamber. Fluid from the fluid chamber is able to permeate the semi-permeable membrane into the osmotic chamber and increase the pressure within the osmotic chamber to deflect a portion of the diaphragm into the reservoir. A difference in solute concentration, the solutes being impermeable to the semi-permeable membrane, between the osmotic chamber and the fluid chamber provides the driving force for the fluid from the fluid chamber permeating the semi-permeable membrane.

In some embodiments, the actuation chamber surrounds the reservoir.

The contact lens can include a manual press area on the outer surface of the periphery of the contact lens and over a portion of the reservoir. The manual press area is configured to bow into the reservoir when the area is pressed.

The contact lens can include at least one or more dissolvable barriers within the reservoir that separates predetermined volumes. A plurality of dissolvable barriers can also be included. In embodiments with a plurality of dissolvable barriers, each barrier has a different rate of dissolution from the other dissolvable barriers. In some embodiments, the predetermined volumes that are separated by at least one barrier are of an equal capacity to one another. Examples of dissolvable barriers that can be used include dissolvable sugar barriers or other known means in the art.

The contact lens can also include a fill port connected with the storage reservoir for refilling the contact lens reservoir with a therapeutic fluid. The fill port can include an elastomer that is configured to self-seal after a piercing needle is withdrawn therefrom.

The contact lens can include a therapeutic liquid within the storage reservoir. The storage reservoir can be disposed in an annulus that surrounds the optical zone. The optical zone can be at least 1, 2, 3, 4, 5, 6, 7, 8, 9, 10, or more millimeters in diameter.

In another aspect, the present invention includes an implantable liquid delivery apparatus including a biocompatible housing, a therapeutic liquid storage reservoir disposed within the housing, a channel from the reservoir to an outlet for dispensing liquid within a subject's body, and a flow regulator connected with the channel.

In some embodiments, the flow regulator includes high-fluidic-resistance channel.

The liquid deliver apparatus can include a one-way valve connected at an output of the reservoir, and a metering volume with a predetermined capacity for a dose of a therapeutic liquid connected with the channel.

The liquid delivery apparatus can include a pressure regulator including a multi-level valve seat, and a floating valve piece configured to mate with the multi-level valve seat. The floating valve piece mates with different levels of the multi-level valve seat depending on pressure, configured to open only between a first predetermined pressure and a second predetermined pressure.

The liquid delivery apparatus can also include a serpentine duct.

The liquid delivery apparatus can include an actuation chamber, and a flexible diaphragm between the actuation chamber and the reservoir. A heating element can be disclosed within the actuation chamber. A phase change material can be included within the actuation chamber. The phase change material being of a substance such that it expands when converting between a solid to a liquid, a solid to a gas, or a liquid to a gas when warmed. The expansion of the phase change causes bowing of a portion of the diaphragm into the reservoir.

The actuation chamber can also include a semi-permeable membrane that divides the actuation chamber into an osmotic chamber and a fluid chamber. Fluid from the fluid chamber is able to permeate the semi-permeable membrane into the osmotic chamber and increase the pressure within the osmotic chamber to deflect a portion of the diaphragm into the reservoir. A difference in solute concentration, the solutes being impermeable to the semi-permeable membrane, between the osmotic chamber and the fluid chamber provides the driving force for the fluid from the fluid chamber permeating the semi-permeable membrane.

In some embodiments, the actuation chamber surrounds the reservoir.

The liquid delivery apparatus can include a manual press area on the outer surface of the periphery of the contact lens and over a portion of the reservoir. The manual press area is configured to bow into the reservoir when the area is pressed.

The liquid delivery apparatus can include at least one or more dissolvable barriers within the reservoir that separates predetermined volumes. A plurality of dissolvable barriers can also be included. In embodiments with a plurality of dissolvable barriers, each barrier has a different rate of dissolution from the other dissolvable barriers. In some embodiments, the predetermined volumes that are separated by at least one barrier are of an equal capacity to one another. Examples of dissolvable barriers that can be used include dissolvable sugar barriers or other known means in the art.

The liquid delivery apparatus can also include a fill port connected with the storage reservoir for refilling the contact lens reservoir with a therapeutic fluid. The fill port can include an elastomer that is configured to self-seal after a piercing needle is withdrawn therefrom.

The contact lens can include a therapeutic liquid within the storage reservoir.

In another aspect, the present invention provides, an ophthalmic eye hydration contact lens apparatus. The eye hydration contact lens apparatus includes a sponge material disposed in an annulus and a water-impermeable shell substantially covering the outer convex surface of the sponge material annulus. The annular sponge material is curved axially to form an inner concave surface and an outer convex surface and includes water-absorbing pores.

The eye hydration contact lens can also include an opening in an outer portion of the shell. The opening exposes a portion of the sponge material through the shell.

In yet another aspect, the present invention provides a dioptric power contact lens apparatus. The diprotic power contact lens includes a contact lens body having a transparent optical zone and an annular periphery outside of the optical zone, a liquid storage reservoir disposed within the periphery of the contact lens body, a lens cavity disposed within the optical zone of the contact lens body, and a transparent liquid within the reservoir or lens cavity, the transparent liquid having a refractive index that is different from that of air. The reservoir and lens cavity are configured such that the transparent liquid flows between the reservoir and the lens cavity depending on an orientation of the contact lens body with respect to gravity, thereby altering a dioptric power of the optical zone.

A further understanding of the nature and the advantages of the embodiments disclosed and suggested herein may be realized by reference to the remaining portions of the specification and the attached drawings.

BRIEF DESCRIPTION OF THE DRAWINGS

FIG. 11 illustrates an osmotic actuation system before fluid release in accordance with an embodiment.

FIG. 12 illustrates an osmotic actuation system after fluid release in accordance with an embodiment.

DETAILED DESCRIPTION

Generally, therapeutic medical liquid dispensing devices are described herein. Particularly described are exemplary contact lens devices to treat dry eyes by supplying a controlled volume of fluid over time to the eye. The devices dispenses a reliable amount of fluid to the eye over extended periods of time. In other embodiments, other fluids delivered can include anti-infective agents, anti-inflammatory drugs, medication for chronic immunomodulation, glaucoma medication, or other known eye medications.

Figure 1:
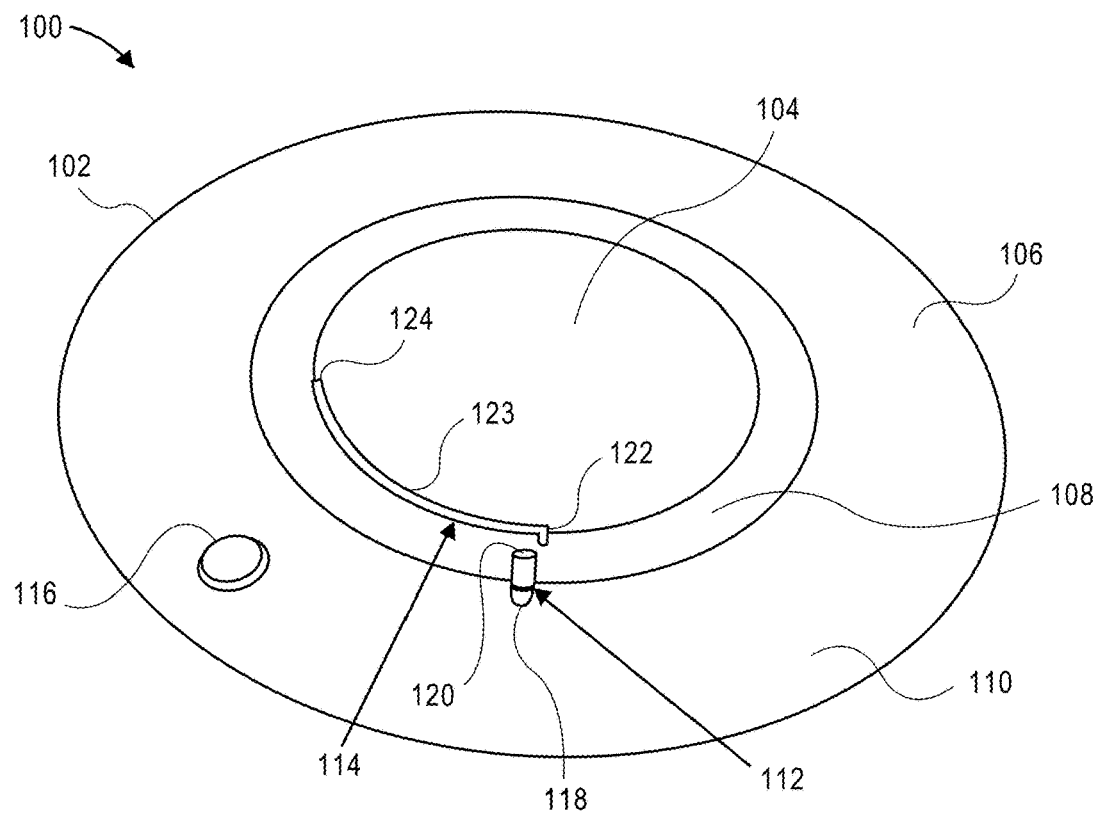
FIG. 1 illustrates a perspective view of an ophthalmic liquid delivery contact lens in accordance with an embodiment.

FIG. 1 illustrates a perspective view of a contact lens in accordance with an embodiment. Contact lens 100 includes a body 102, a transparent optical zone 104, and an annular periphery 110. The annular periphery 110 further includes a metering volume 108 and a therapeutic liquid storage reservoir 106. Liquid travels from the reservoir 106 through an opening 118 of a one-way valve 112 and out an outlet 120 into the metering volume 108. From the metering volume 108, the liquid travels to an opening 122 and through a channel 123 that includes a flow regulator 114 and out of an outlet 124 and into the eye. Contact lens 100 also includes a fill port 116 for refilling the reservoir 106 when fluid has been depleted.

The reservoir 106 is a hollow cavity within the contact lens that allows for fluid storage. The total liquid storage volume of reservoir is variable and dependent on the needs of the particular user. For example, the reservoir volume can be fabricated to accommodate users requiring larger volume of fluid delivery or a small volume of liquid delivery throughout the course of wearing the contact lens. At times, higher concentrations of drugs delivered to the eye requires a smaller reservoir, while lower concentration of drugs delivered to the eye requires a larger reservoir. In some embodiments, the volume of the fluid reservoir is not dependent on the concentration of the drug or fluid delivered. The reservoir can be made from any suitable biocompatible material including, but not limited to, silicon hydrogel, polymethyl methacrylate, silicone acrylate, or parylene.

The metering volume 108 is a separate cavity within the contact lens. In some embodiments, the metering volume is used to supply a precise and known amount of fluid to the eye at a given time. In some embodiments, the metering volume is used to control the continuous flow rate of the fluid into the eye. The metering volume can be larger than, equal to, or smaller than the volume of the reservoir 106, depending on the needs and specific design of the contact. For example, when delivering high concentrations of drug, the metering volume can be smaller. When delivering low concentrations of drug, the metering volume can be larger. In some embodiments, the size of the metering volume is not dependent on the concentration of the drug or fluid delivered.

The flow regulator 114 and channel 123 can be fabricated to meet any flow rate or delivery scheduled desired. For example, the flow regulator can be fabricated to allow for a continuous and highly controlled delivery of fluid from the contact lens into the eye through a given time period. Alternatively, the flow regulator can be fabricated to accommodate a discontinuous fluid delivery schedule where a known amount of fluid is dispensed into the eye at specific intervals.

The fill port 116 for refilling the reservoir can be any suitable self-sealing elastomer including silicone rubber and polyurethane. The fill port can be accessed by a needle or any other suitable puncturing device that allows for resealing of the fill port after puncture and withdrawal of the puncturing device. The fill port is generally located at a distal portion of the contact lens, away from the optical zone.

Figure 2A:
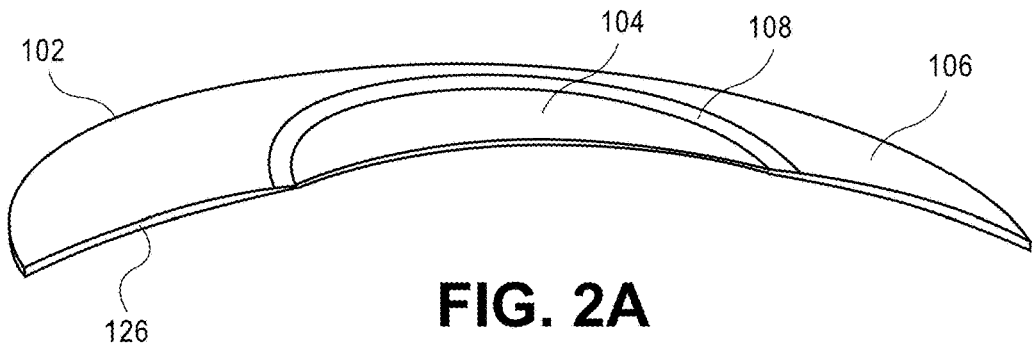
FIG. 2A illustrates a cross sectional view of the ophthalmic liquid delivery contact lens shown in FIG. 1.

FIG. 2A illustrates a cross sectional view of the contact lens shown in FIG. 1. The contact lens body 102 comprises the transparent optical zone 104, the metering volume 108, and the reservoir 106. Therapeutic fluid 126 dispensed by the contact lens is stored in the space show in the reservoir 106.

Figure 2B:
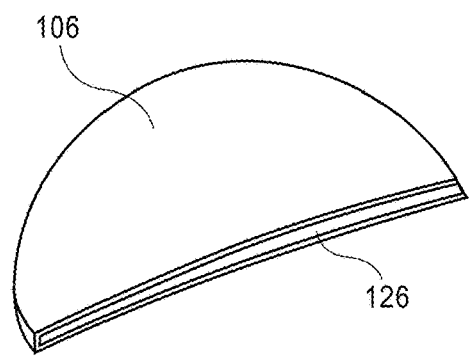
FIG. 2B shows a zoomed in view of the ophthalmic liquid delivery contact lens cross section shown in FIG. 2A.

FIG. 2B shows a zoomed in view of the ophthalmic liquid delivery contact lens cross section show in FIG. 2A. This view highlights storage space of the fluid 126 in the reservoir 106.

Figure 3:
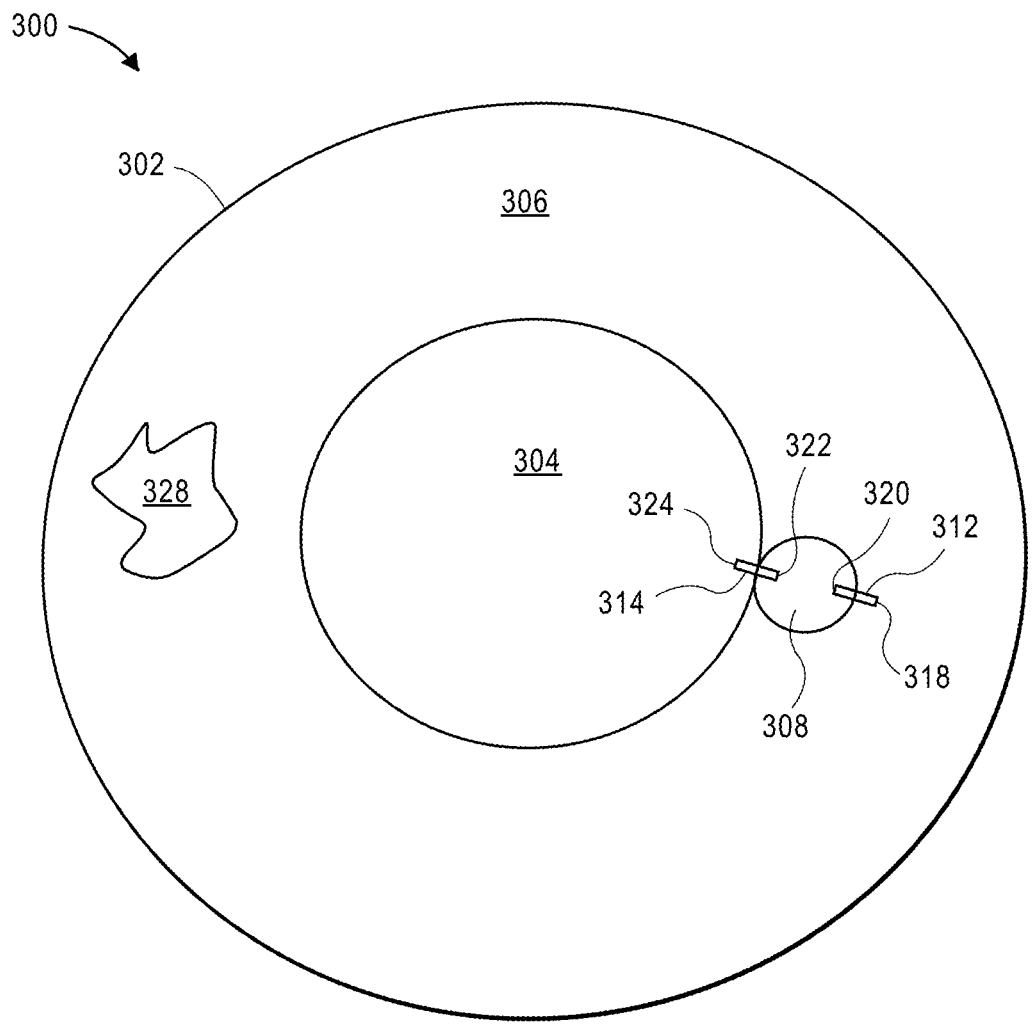
FIG. 3 illustrates an ophthalmic liquid delivery contact lens in accordance with an embodiment.

FIG. 3 illustrates an ophthalmic liquid delivery contact lens in accordance with an embodiment. Contact lens 300 includes a body 302, a transparent zone 304, a therapeutic liquid storage reservoir 306, and a metering volume 308. Liquid travels from the reservoir 306 into an opening 318 of a one-way valve 312 and out an outlet 320 into the metering volume 308. From the metering volume 308, the fluid travels into an opening 322 of a flow regulator 314 and out an outlet 324 and into the eye. Contact lens 300 also includes a manual press area 328. Pressure is applied to the manual press area 328 to force liquid from the reservoir 306 into the metering volume 308.

In some embodiments, the manual press area 328 is marked for easy identification by the user. In some embodiments, the manual press area is marked with a change in color. The manual press area 328 can be made from any biocompatible material that can be accommodated within the eye. In some embodiments, the manual press area is made from the same material as the rest of the contact lens. In some embodiments, the manual press area is made from a soft material such as silicon hydrogel. In some embodiments, the manual press area is made from a hard material such as polymethyl methacrylate. The thickness of the outer surface of the contact lens at the manual press area can be modified to accommodate the pressure applied by the user. For example, the thickness of the manual press area can be thickened or thinned depending on the material used.

In the embodiment shown in FIG. 3, the metering volume 308 is isolated from the manual press area 328 by positioning the two on opposite sides of the contact lens. In embodiments containing a manual press area and a metering volume, the metering volume is generally separated from the manual press area to avoid external pressure being applied to the metering volume. In some instances, the manual press area and metering volume are on opposite sides of the transparent optical zone. Although FIG. 3 shows the metering volume substantially smaller than FIG. 1, the size of the metering volume for embodiments containing a manual press area is dependent on the specific needs of delivery. As such, the metering volume can be smaller than, equal to, or larger than the fluid reservoir.

Figure 4:
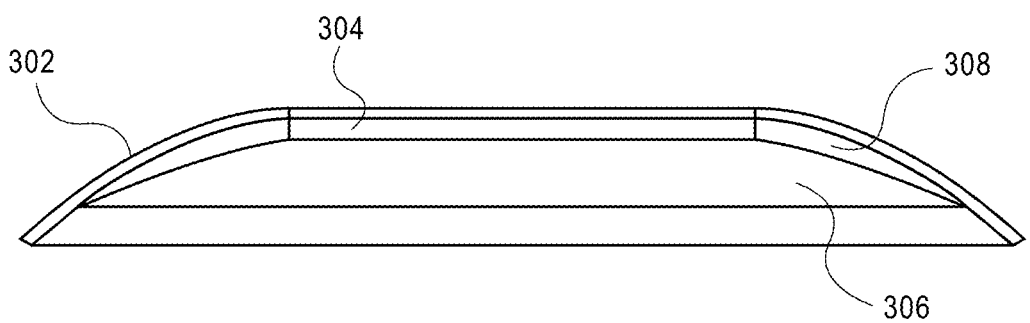
FIG. 4 illustrates a cross sectional view of an ophthalmic liquid delivery contact lens shown in FIG. 3.

FIG. 4 illustrates a cross sectional view of an ophthalmic liquid delivery contact lens shown in FIG. 3. This cross section shows the contact lens body 302 with the transparent zone 304 surrounded by the reservoir 306. The metering volume 308 is shown on one side of the transparent zone 304.

Although FIGS. 1-4 shows a single one-way valve separating the metering volume and the reservoir, two, three, four, or more valves may also be employed. In some embodiments the valve is a check valve. In some embodiments the valve is electronically active. In some embodiments, the valve is a band pass valve. In some embodiments a high-resistance fluidic connection between the reservoir and the metering volume limits the speed that the metering volume fills. For example, channel 123 can be packed with beads or have a plurality of fins that slow liquid from flowing. Alternatively, in some embodiments, there may be no valves separating the metering volume and the reservoir.

The contact lenses shown may be made out of materials such as silicon hydrogel, polymethylmethacrylate, hydroxethylmethacrylate, or any other known materials in the art.

In certain embodiments, the inner diameter of the contact lens, the transparent optical zone, is at least 4.0 mm to 7.0 mm to 9.00 mm. In some embodiments, the transparent optical zone contains an optical area that can be used for correction of ametropia, cosmetic/color correction, treatment of colorblindness, and/or ultraviolet (UV) absorbance.

"About" includes within a tolerance of ±0.01%, ±0.1%, ±1%, ±2%, ±3%, ±4%, ±5%, ±8%, ±10%, ±15%, ±20%, ±25%, or as otherwise known in the art.

The term "lens" includes a device having a non-constant thickness to converge or diverge light passing therethrough as well as device having a constant thickness that does not converge or diverge light passing therethrough. A portion of the lens may be opaque or translucent.

In some embodiments, the driving force of liquid delivery to the eye is in equilibrium between the reservoir, the metering volume, and the eye. In some embodiments, the driving force is the pressure cause by blinking. In some embodiments, the driving force is the pressure caused by manual pressing on a predetermined location of the contact lens. In some embodiments, the driving force is the pressure from an actuation system coupled to the contact lens.

The flow rate (dosing) of the fluid into the eye can be controlled by a flow regulator. The flow regulator can be a suitable metering valve/flow regulator/pressure regulator. In some embodiments, one or more metering valves/flow regulators/pressure regulators can be coupled to achieve the desired flow rate of fluid into the eye. In some embodiments, the flow regulator can be a high-fluidic-resistance channel. A high-fluidic-resistance channel can be any channel with a high resistance including channels with small apertures or a channels with solid material that increases the resistance of the fluid passing through. In some embodiments, the fluidic resistor/pressure regulator is as shown in FIGS. 5 and 6.

Figure 5:
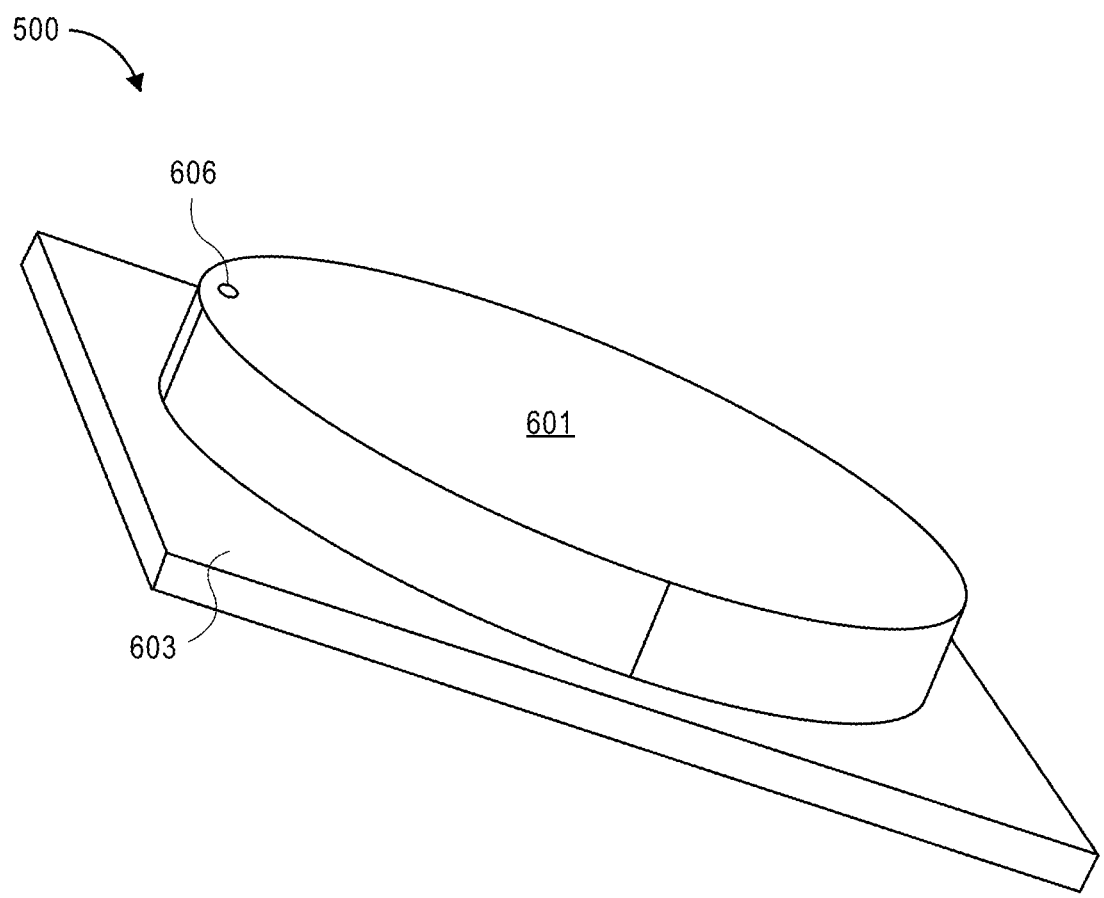
FIG. 5 illustrates a fluidic resistor/pressure regulator in accordance with an embodiment.
Figure 6:
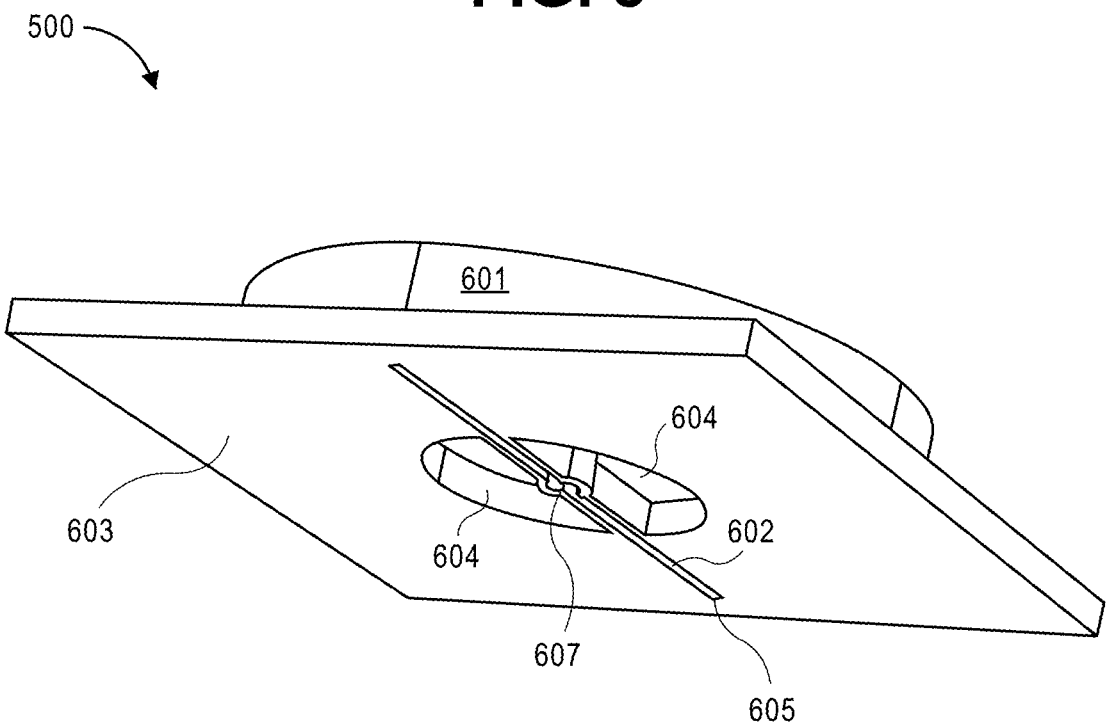
FIG. 6 illustrates the fluidic resistor/pressure regulator shown in FIG. 5 rotated 90°.

FIGS. 5 and 6 illustrates a fluidic resistor/pressure regulator in accordance with an embodiment. Fluidic resistor 500 includes a top 601, a channel 602, and a bottom 603. The bottom 603 includes two cut out C-shaped halves 604 adjacent to the channel. Fluid flows in through the inlet 605, continues through channel 602 and out through the outlet 606. As the fluid passes through the channel 602, there is a flexible diaphragm 607 that deflects into the path of the channel when the pressure at the top 601 is greater than the pressure at the bottom 603. The amount of deflection depends on the size of the difference between the two pressures (pressure from the top 601 and pressure from the bottom 603). This deflection pinches off the channel 602, which increases the resistance in the channel and results in decreased pressure in top 601. When the pressure on top 601 is low, then the channel is not pinched as much, resulting in a pressure increase in top 601. The device keeps the difference in pressure between the top 601 and bottom 603 constant.

In some embodiments, the resistance in the channel 602 can be held constant, allowing for a constant, controlled flow rate.

In some embodiments, serpentine ducts are etched into a contact lens to deliver a fluid to the eye.

Figure 7:
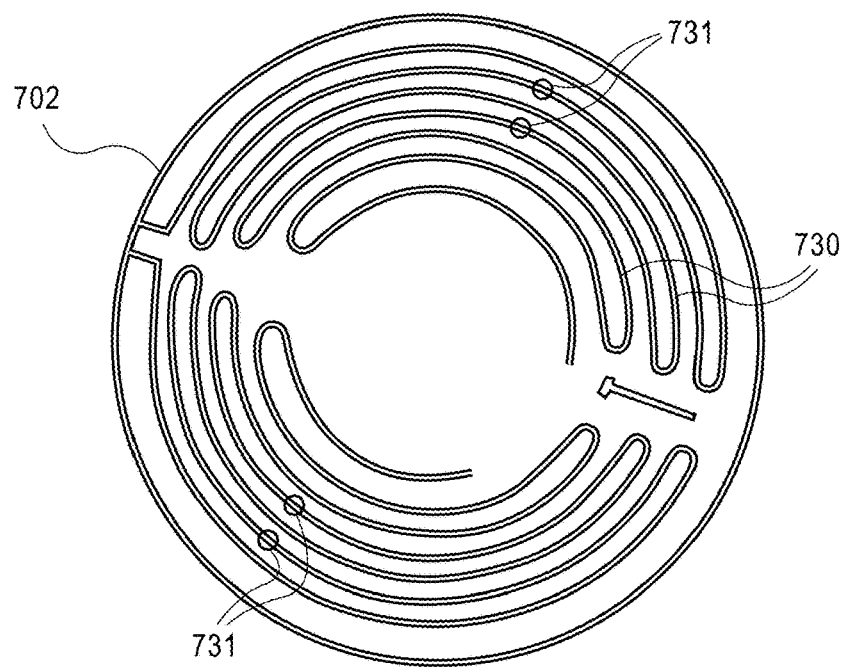
FIG. 7 illustrates an ocular contact lens with a serpentine duct in accordance with an embodiment.

FIG. 7 illustrates an ocular contact lens with a serpentine duct in accordance with an embodiment. Contact lens body 702 contains serpentine ducts 730 that extend tangentially to the contact lens body. Preloaded fluid travels through serpentine ducts to openings near the central optical zone and into the eye. Also shown within the serpentine ducts 730 are dissolvable barriers 731 that control release of a predetermined volume of fluid by blocking the fluid within the serpentine duct. After an amount of time, each barrier dissolves, allowing for free flow of the fluid through the serpentine duct, out the exit, and into the eye. For example, a first barrier may dissolve after 2 hours, a second barrier after 4 hours, and a third barrier after 6 hours.

In some embodiments, one or more dissolvable barriers are included to block the flow of a predetermined volume of fluid. After an amount of time, the barriers dissolve allowing the predetermined volume of fluid to flow. When one or more dissolvable barriers are used, the each dissolvable barrier might dissolve at a different rate. Any suitable dissolvable material can be used.

Figure 8:
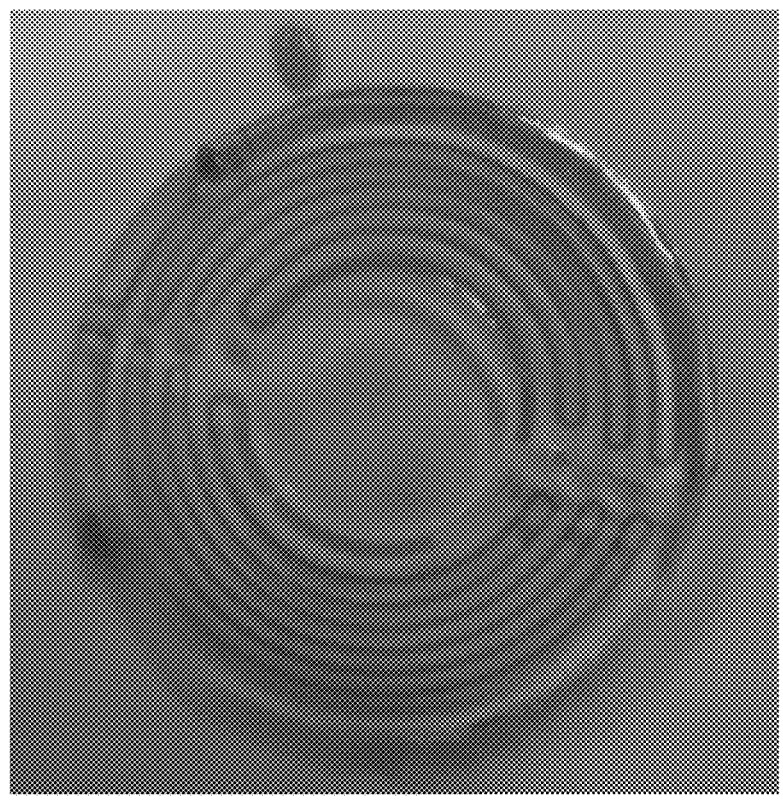
FIG. 8 is a picture of a fabricated ocular contact lens with a serpentine duct in accordance with an embodiment.

FIG. 8 is a picture of a fabricated ocular contact lens with a serpentine duct in accordance with an embodiment. The serpentine duct can be etched into a contact lens using reactive-ion etching, wet etching, or any other etching techniques known in the art.

In some embodiments, the flow rate within the serpentine ducts is regulated by a flow regulator connected to the channel. In some embodiments, the flow rate within the serpentine ducts is limited by the pressure applied through a user blinking. In some embodiments, the dosing rate within the serpentine ducts is regulated by dissolvable barriers.

In another aspect, the present invention provides for implantable liquid delivery apparatuses that can be used to deliver fluids to targeted locations within a subject's body. The fluids dispensed by these systems can be any therapeutically effective fluid. In some embodiments, the actuation systems described herein are used as an implantable drug delivery device. In some embodiments, the actuation systems described herein can be coupled with the contact lenses described herein to provide an external pressure and a driving force to deliver all the liquid from the contact into the eye.

Figure 9:
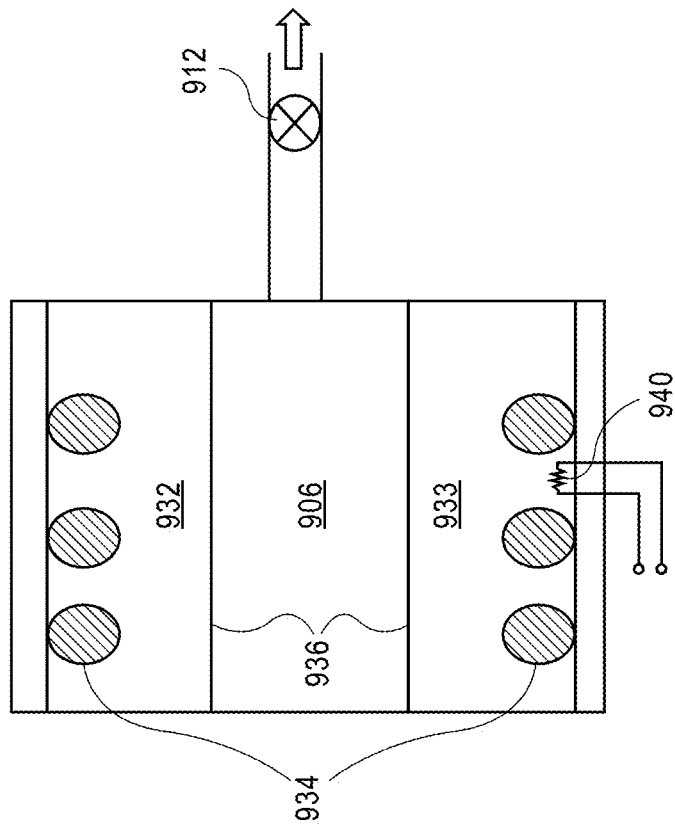
FIG. 9 illustrates a phase change actuation system before fluid release in accordance with an embodiment.

FIG. 9 illustrates a phase change actuation system before fluid release in accordance with an embodiment. The phase change actuation system consists of a reservoir 906 that is surrounded by two actuation chambers 932 and 933. The barriers separating the reservoir 906 and the two actuation chambers 932 and 933 are flexible diaphragms 936. In each actuation chamber there is one or more phase change materials 934 that expand when changing phase (e.g. melt, evaporate, sublimate) when a target temperature is reached, thereby increasing pressure. Heating element 940 can be used to expedite the phase change by warming the actuation chamber. Upon heating and phase change, flexible diaphragms 936 bow into the reservoir, increasing pressure within the reservoir until the valve 912 is opened. This forces fluid to be delivered to the target side to the right of the figure.

Figure 10:
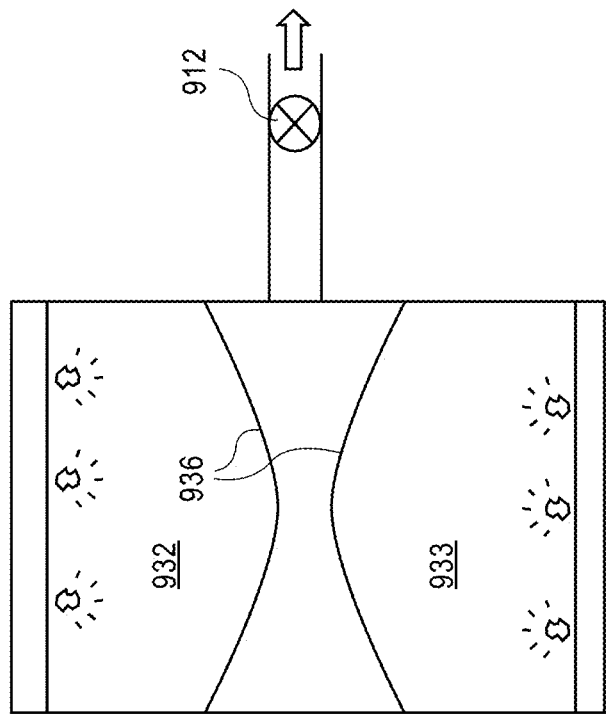
FIG. 10 illustrates a phase change actuation system after fluid release in accordance with an embodiment.

FIG. 10 illustrates a phase change actuation system after fluid release in accordance with an embodiment.

Any material that expands upon phase change within the desired temperature range of the device is a suitable phase change material. In some embodiments, the phase change occurs within a temperature range in the normal temperature range encountered during a daily life of the patient (e.g., 50° F. and 160° F., more specifically between 70° F. and 120° F.). In some embodiments, the phase change occurs from a built in heating element. By using different phase change materials, the rate of fluid delivery can be tailored to meet specific needs.

FIGS. 11 and 12 illustrates an osmotic actuation system before (FIG. 11) and after (FIG. 12) fluid release in accordance with an embodiment. The osmotic actuation system consists of a reservoir 1106 and an adjacent actuation chamber 1132. Reservoir 1106 and actuation chamber 1132 are separated by a flexible diaphragm 1136. The actuation chamber 1132 consists of an osmotic chamber 1138 and a fluid chamber 1140. The osmotic actuation system also includes a one way valve 1112. The osmotic chamber 1138 and the fluid chamber 1140 are separated by a semipermeable membrane 1137. The semipermeable membrane 1137 allows for fluid (solvent) to pass through, but does not allow solutes. The osmotic chamber 1138 contains a higher solute concentration than the fluid chamber 1140. The resulting osmotic pressure causes fluid 1142 (solvent) to flow from the fluid chamber 1140 through the semipermeable membrane 1137 into the osmotic chamber 1138. The influx in fluid in the osmotic chamber causes the flexible diaphragm 1136 to bow into the reservoir 1106 forcing fluid to pass through the one way valve 1112.

FIG. 12 illustrates an osmotic actuation system after fluid release in accordance with an embodiment.

"Permeability" of a material is typically in relation to a size of substance of interest. A Stokes-Einstein radius or a Stokes diameter is a measure of the diffusion properties of a substance. A "Stokes diameter" is an equivalent diameter of a hard sphere that a molecule possesses in terms of its diffusion rate. A molecule can pass through thin materials with pores that have a Stokes diameter that is about 1 to about 5 times the Stokes diameter of the molecule.

In some embodiments, the osmotic and phase change actuation systems are coupled into a single system.

Figure 14:
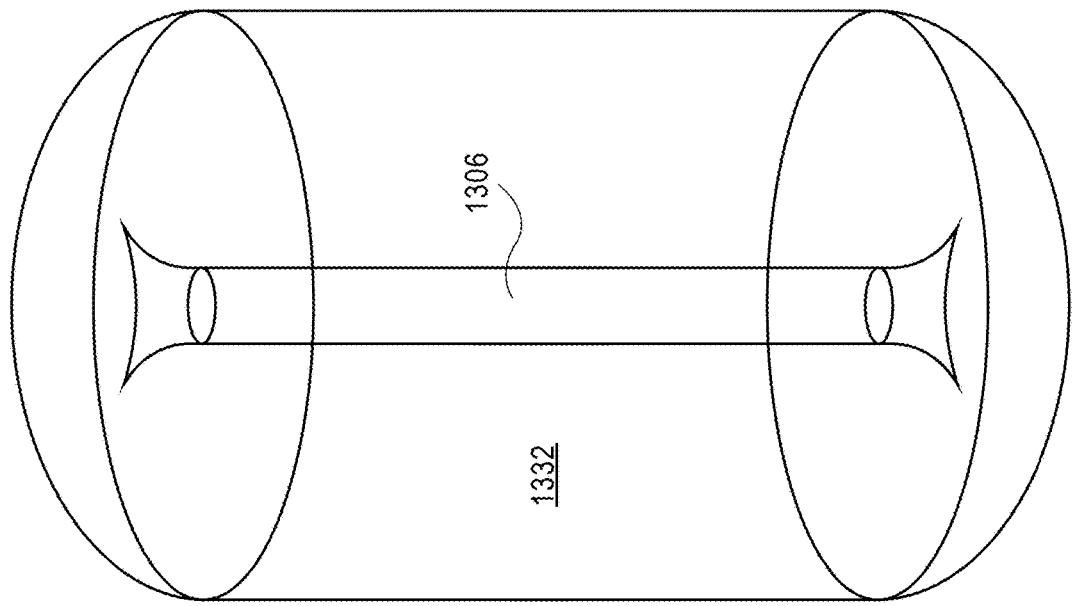
FIG. 14 illustrates an actuation system after fluid release in accordance with an embodiment. In this embodiment, the actuation chamber surrounds the reservoir.
Figure 13:
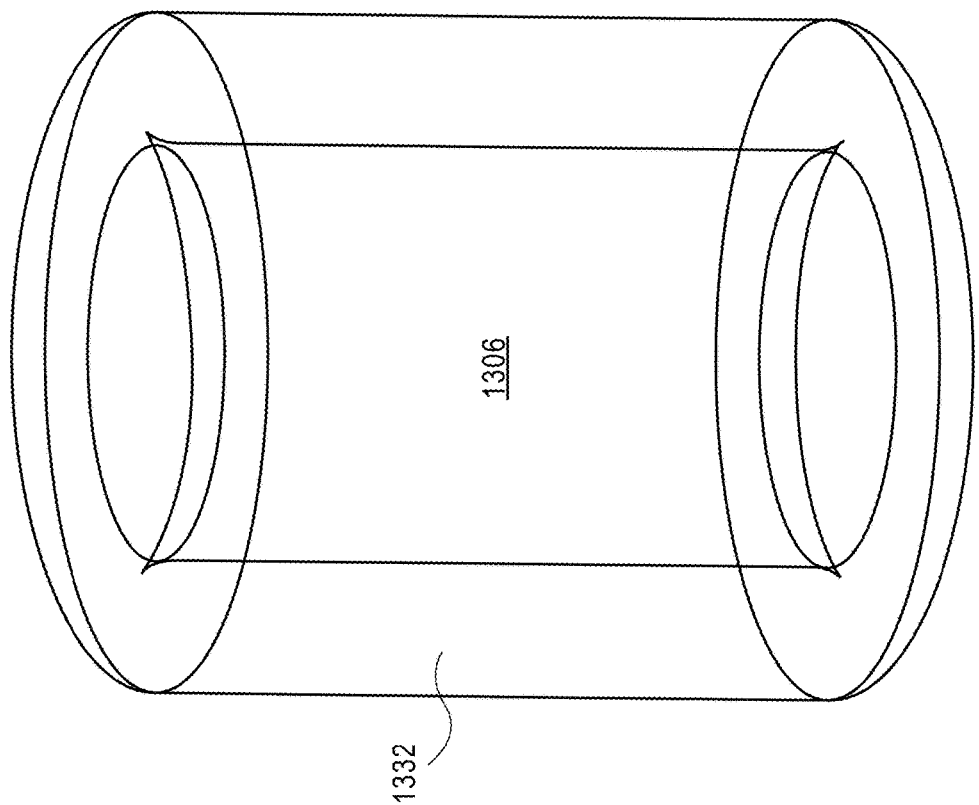
FIG. 13 illustrates an actuation system before fluid release in accordance with an embodiment. In this embodiment, the actuation chamber surrounds the reservoir.

FIG. 13 illustrates an actuation system before fluid release in accordance with an embodiment, and FIG. 14 illustrates an actuation system after fluid release in accordance with an embodiment. In this embodiment, the actuation chamber 1332 surrounds the reservoir 1306. Fluid release is instigated through the expansion of actuation chamber 1332 which decreases the volume of the reservoir 1306, forcing fluid release from the reservoir. In some embodiments, the actuation chamber shown in FIGS. 13 and 14 is incorporated into the contact lens devices described above. By surrounding the reservoir, actuation chamber can rely less on external forces to keep it pressed against the reservoir.

In another aspect, the present invention provides of an ophthalmic eye hydration contact lens apparatus.

Figure 15:
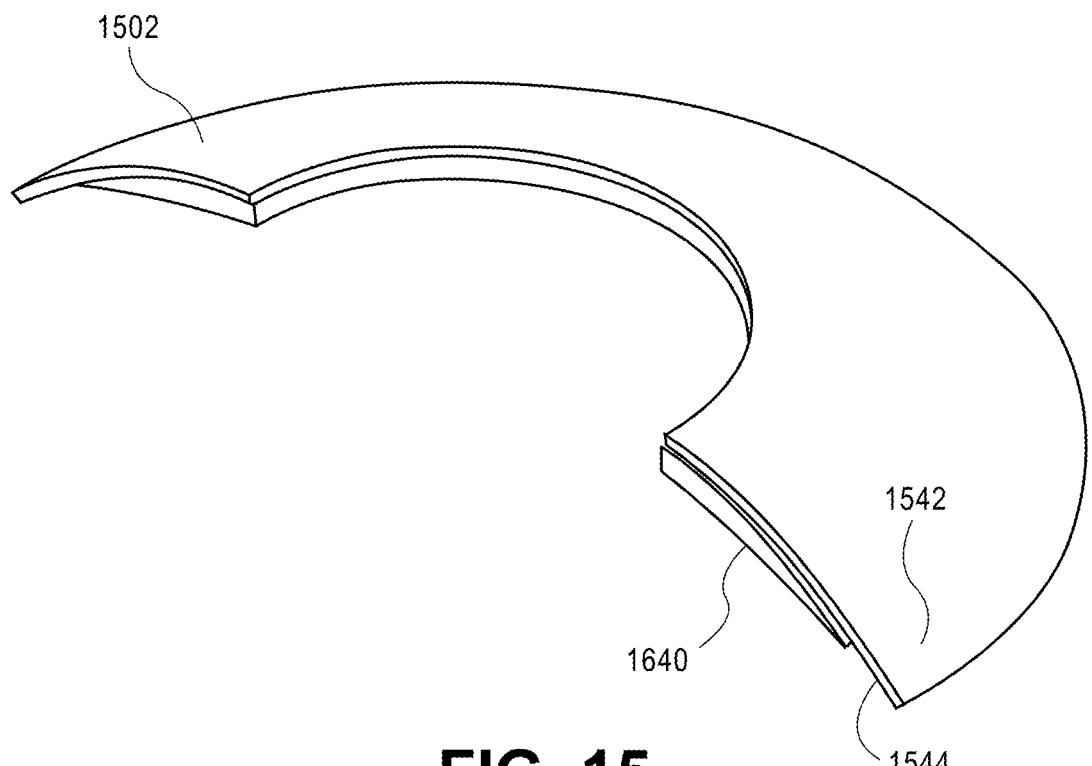
FIG. 15 illustrates a cross sectional view of an ophthalmic eye hydration contact lens apparatus in accordance with an embodiment.

FIG. 15 illustrates a cross sectional view of an ophthalmic eye hydration contact lens apparatus in accordance with an embodiment. Contact lens body 1502 contains a convex side and a concave side 1544. The convex side is defined by a water impermeable shell 1542. The concave side 1544 of the contact lens contains a sponge material 1640.

Figure 16:
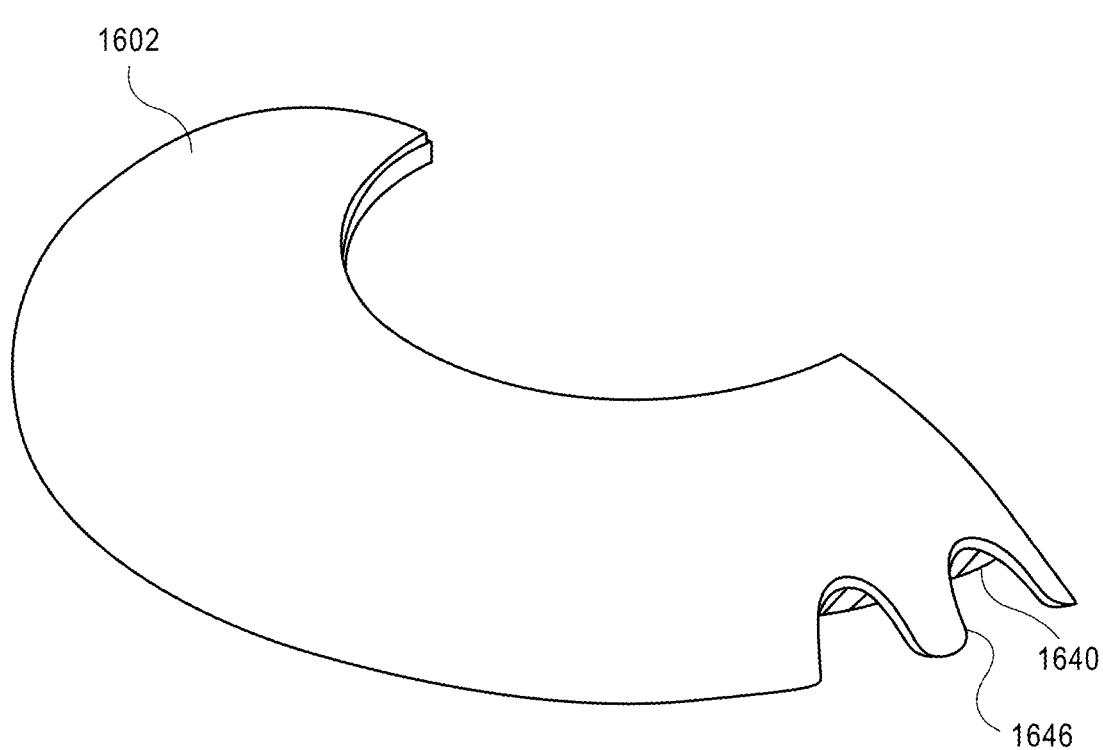
FIG. 16 illustrates a cross sectional view of another half of the ophthalmic eye hydration contact lens apparatus shown in FIG. 15 with an opening in the outer portion of the shell exposing a portion of the sponge material.

FIG. 16 illustrates a cross sectional view of another half of the ophthalmic eye hydration contact lens apparatus shown in FIG. 15. The contact lens body 1602 contains an opening 1646 in the outer portion of the shell exposing a portion of the sponge material 1640.

In some embodiments, the sponge material stores liquid and prevents it from exiting the eye. Upon blinking a percentage of the liquid is released onto the cornea. After blinking, excess liquid is absorbed back into the sponge reservoir. In some embodiments the absorbing material is impregnated with an anti-infective such as an antibiotic. In some embodiments, the opening in the outer portion of the shell allows liquid to naturally flow into the sponge material. In some embodiments the sponge material can be high-density polyvinyl acetate, cellulose, or any known material in the art. In some embodiments the sponge material contains an inner concave surface and outer convex surface. In some embodiments the sponge material contains an inner planar surface and an outer convex surface.

The invention has been described with reference to various specific and illustrative embodiments. However, it should be understood that many variations and modifications may be made while remaining within the spirit and scope of the following claims.

In another aspect, the present invention provides a variable diprotic power contact lens apparatus. This contact lens has a body with a transparent optical zone with a lens cavity disposed within the optical zone and a peripheral reservoir. The peripheral reservoir stores a transparent fluid with a different refractive index. When the orientation of the contact lens body is changed with respect to gravity, liquid can flow between the reservoir and the lens cavity. As the fluid enters the lens cavity, the optical power of the lens also changes. When the orientation of the contact lens body is returned to its previous state, the fluid flows out of the lens cavity and the optical power of the lens returns to its initial state.

The invention has been described with reference to various specific and illustrative embodiments. However, it should be understood that many variations and modifications may be made while remaining within the spirit and scope of the following claims.

What is claimed is:

1. An ophthalmic liquid delivery contact lens apparatus comprising:
   a contact lens body having a central optical zone and an annular periphery outside of the central optical zone;
   a sponge material disposed in the annular periphery, the sponge material curved axially to form an inner concave surface and an outer convex surface, the sponge material comprising high-density polyvinyl acetate or cellulose forming liquid absorbing pores; and
   a liquid-impermeable shell substantially covering the outer convex surface of the sponge material annulus;
   a therapeutic liquid storage reservoir disposed within the annular periphery of the contact lens body; and
   a fill port connected with the therapeutic liquid storage reservoir, wherein the fill port comprises an elastomer configured to self-seal after a piercing needle is withdrawn therefrom.

2. The ophthalmic liquid delivery contact lens apparatus of claim 1 further comprising: a one-way valve connected at an output of the therapeutic liquid storage reservoir; wherein fluid is able to flow through the one-way valve into the sponge material to continually restore percentage of liquid stored within the sponge material.

3. The ophthalmic liquid delivery contact lens apparatus of claim 1 further comprising:
   an opening in an outer portion of the liquid-impermeable shell, the opening exposing a portion of the sponge material through the liquid-impermeable shell.

4. The ophthalmic liquid delivery contact lens apparatus of claim 3 wherein the opening extends to a circumference of the liquid-impermeable shell.

5. The ophthalmic liquid delivery contact lens apparatus of claim 3 further comprising:
   one or more additional openings in the outer portion of the liquid-impermeable shell.

6. The ophthalmic liquid delivery contact lens apparatus of claim 1 further comprising: a manual press area on an outer surface of the annular periphery and over a portion of the therapeutic liquid storage reservoir, the manual press area configured to bow into the therapeutic liquid storage reservoir.

7. The ophthalmic liquid delivery contact lens apparatus of claim 1 wherein the sponge material is impregnated with an anti-infective such as an antibiotic.

8. The ophthalmic liquid delivery contact lens apparatus of claim 1 further comprising: a therapeutic liquid within the therapeutic liquid storage reservoir.

9. The ophthalmic liquid delivery contact lens apparatus of claim 1 wherein the central optical zone is at least 4.0 millimeters in diameter.

10. The ophthalmic liquid delivery contact lens apparatus of claim 1 wherein the central optical zone comprises a lens with optical power.

11. The ophthalmic liquid delivery contact lens apparatus of claim 1, wherein the central optical zone comprises an opening.

12. The ophthalmic liquid delivery contact lens apparatus of claim 1, wherein the central optical zone comprises an optical area made with a material suitable for at least one of: ametropia correction, cosmetic correction, color correction, colorblindness treatment, or ultraviolet absorbance.

13. The ophthalmic liquid delivery contact lens apparatus of claim 1, wherein the sponge material is configured to release liquid to a cornea of a user when blinking and absorb excess liquid back after the blinking.

14. The ophthalmic liquid delivery contact lens apparatus of claim 1, further comprising:
    a channel from the therapeutic liquid storage reservoir; and
    a flow regulator connected with the channel.

15. The ophthalmic liquid delivery contact lens apparatus of claim 1, wherein the flow regulator includes a high-fluidic-resistance channel.

16. The ophthalmic liquid delivery contact lens apparatus of claim 15, wherein the high fluidic resistance channel includes a serpentine duct.

17. The ophthalmic liquid delivery contact lens apparatus of claim 1, further comprising: a dissolvable barrier within the serpentine duct.

18. The ophthalmic liquid delivery contact lens apparatus of claim 1, wherein the flow regulator includes a metering valve.

19. The ophthalmic liquid delivery contact lens apparatus of claim 1, wherein the flow regulator includes a pressure regulator.

20. The ophthalmic liquid delivery contact lens apparatus of claim 1, wherein the therapeutic liquid storage reservoir comprises parylene or silicone rubber.

* * * * *